United States Patent
Tu et al.

(10) Patent No.: US 10,766,841 B2
(45) Date of Patent: Sep. 8, 2020

(54) METHOD OF PREPARING BIO-POLYOLS FROM EPOXIDIZED FATTY ACID ESTERS

(71) Applicant: CPC Corporation, Taiwan, Kaohsiung (TW)

(72) Inventors: You-Liang Tu, Kaohsiung (TW);
Ya-Shiuan Lin, Kaohsiung (TW);
Ming-Tsang Tsai, Kaohsiung (TW);
Chiu-Ping Li, Kaohsiung (TW)

(73) Assignee: CPC Corporation, Kaohsiung (TW)

( * ) Notice: Subject to any disclaimer, the term of this patent is extended or adjusted under 35 U.S.C. 154(b) by 0 days.

(21) Appl. No.: 16/662,321

(22) Filed: Oct. 24, 2019

(65) Prior Publication Data

US 2020/0148614 A1    May 14, 2020

(30) Foreign Application Priority Data

Nov. 13, 2018  (TW) .................... 107140293

(51) Int. Cl.
| | | |
|---|---|---|
| *C07C 29/48* | (2006.01) | |
| *C08G 18/32* | (2006.01) | |
| *C07C 27/34* | (2006.01) | |
| *B01J 31/02* | (2006.01) | |
| *C07C 69/675* | (2006.01) | |
| *C07D 303/42* | (2006.01) | |

(52) U.S. Cl.
CPC ........... *C07C 29/48* (2013.01); *B01J 31/0298* (2013.01); *C07C 27/34* (2013.01); *C07C 69/675* (2013.01); *C08G 18/3206* (2013.01); *B01J 2231/005* (2013.01); *B01J 2531/002* (2013.01); *C07D 303/42* (2013.01)

(58) Field of Classification Search
CPC ....... C07C 29/48; C07C 69/675; C07C 27/34; C07D 303/42; B01J 31/2098; B01J 2231/005; C08G 18/3206
See application file for complete search history.

(56) References Cited

U.S. PATENT DOCUMENTS

| | | | | |
|---|---|---|---|---|
| 6,107,433 A | * | 8/2000 | Petrovic | C07D 303/42 528/1 |
| 6,433,121 B1 | | 8/2002 | Petrovic et al. | |
| 9,216,940 B2 | | 12/2015 | Curtis et al. | |
| 9,556,403 B2 | * | 1/2017 | Cramail | C07C 67/03 |
| 10,093,636 B2 | * | 10/2018 | Tu | C07D 301/12 |
| 2003/0088054 A1 | * | 5/2003 | Chasar | C07C 67/31 528/405 |
| 2008/0108782 A1 | * | 5/2008 | Kazemizadeh | C09D 175/04 528/365 |
| 2010/0267925 A1 | * | 10/2010 | Abraham | C07C 67/03 528/361 |

FOREIGN PATENT DOCUMENTS

| | | | |
|---|---|---|---|
| CN | 101125912 | A | 2/2008 |
| CN | 100390128 | C | 5/2008 |
| CN | 100465152 | C | 3/2009 |
| CN | 101735175 | A | 6/2010 |
| CN | 102787007 | A | 11/2012 |
| CN | 104341297 | A | 2/2015 |
| CN | 104341297 | * | 6/2015 |
| CN | 104672113 | A | 6/2015 |
| CN | 104725210 | A | 6/2015 |

OTHER PUBLICATIONS

Cai, S. et al., Epoxidation of unsaturated fatty acid methyl esters in te presence of SO3H-functional Bronsted Acidic Ionic Liquid as catalyst, Chinese Journal of Chemical Engineering, 19(1), pp. 57-63 (Year: 2011).*

* cited by examiner

*Primary Examiner* — Yate' K Cutliff
(74) *Attorney, Agent, or Firm* — Alan D. Kamrath; Mayer & Williams PC

(57) ABSTRACT

A method of preparing bio-polyols from epoxidized fatty acid esters, wherein the bio-polyols are synthesized via hydroxylation with epoxidized fatty acid esters and ring-opening reagent, using the acidic ionic liquids as catalysts. The bio-polyols are used to synthesize bio-polyurethane and bio-polyurethane foams. The acidic ionic liquids in this process is used in esterification, epoxidation, and ring-opening reaction to synthesize bio-polyols. The ionic liquids catalysts have several advantages such as easy to separate, reusable, and may reduce pollution.

12 Claims, No Drawings

METHOD OF PREPARING BIO-POLYOLS FROM EPOXIDIZED FATTY ACID ESTERS

FIELD OF THE INVENTION

The present invention relates to a method of preparing bio-polyols from epoxidized fatty acid esters by which the bio-polyols are made of raw material in a green manufacturing process.

BACKGROUND OF THE INVENTION

Bio-polyols are made of vegetable oil and are epoxidized and hydroxylated by using unsaturated double bond, wherein epoxy is ring-opening hydroxylated by strong acids, such as sulfuric acid (as disclosed in U.S. Pat. No. 9,216,940), boron trifluoride ($BF_3$), tetrafluoroboric acid (as disclosed in U.S. Pat. No. 6,433,121), phosphate (as disclosed in US Patent No. CN104672113). However, such strong acids has high causticity, causes carbonization of raw materials or products, is non-recyclable. In addition, strong alkali solution is used after epoxy is ring-opening hydroxylated to increase manufacture cost and produce waste water, wherein boron trifluoride makes smokes in humid air and is toxic. To overcome such a problem, solid acid catalyst (as disclosed in CN 104725210) is hydroxylated and is synthesized from zeolite, kaolin, and montmorillonite to produce polyols.

Alternatively, inorganic catalyst (such as alkali metal hydroxide or alkali metal alkoxide) or organic alkali (such as organic amine compound) is ring-opening hydroxylated as disclosed in CN Publication Nos. CN 100465152, CN 100390128, and CN101125912, wherein corrosion to reaction tank or pipes is evitable by using organic alkali, but the organic alkali is neutralized by ways acidic substances of and is absorbed by using adsorbent, thus increasing cost. Furthermore, the catalyst is not recycled.

Acidic ionic liquid is applicable for catalytic esterification, transesterification, epoxidation (as disclosed in CN Publication Nos. CN 101735175 and CN 102787007), and ring-opening hydroxylation (as disclosed in CN Publication No. CN 104341297) to be recyclable after reacting process.

When above-mentioned treatment takes long time, the patient will feel uncomfortable, because conducting current repeatedly.

The present invention has arisen to mitigate and/or obviate the afore-described disadvantages.

SUMMARY OF THE INVENTION

The primary aspect of the present invention is to provide a method of preparing bio-polyols from epoxidized fatty acid esters by which the bio-polyols are made of raw material in a green manufacturing process To obtain above-mentioned aspects, a method of preparing bio-polyols from epoxidized fatty acid esters provided by the present invention contains steps of:

replacing amphoteric compound by using alkyl sulfonic acid, wherein the alkyl sulfonic acid are synthesized with Brønsted strong acid to produce Brønsted acid IL, a molar ratio of the alkyl sulfonic acid and the Brønsted strong acid is within 1.0 to 1.5; mixing the epoxidized fatty acid esters and the Brønsted acid IL at a predetermined ratio, adding alcohols for using as ring-opening reagent, thus producing reaction solution, wherein the reaction solution is heated within a temperature of 30° C. to 100° C. for 1 to 24 hours to cause ring-opening hydroxylation, wherein a molar ratio of the alcohols and the epoxidized fatty acid esters is within 4 to 20, and a molar ratio of the Brønsted acid IL and the epoxidized fatty acid esters is within 0.01 to 0.15; and extracting and layering the reaction solution by using deionized water to acquire upper-layer solution and lower-layer solution, wherein the lower-layer solution consists of ionic liquid which is concentrated and dried to recycle reusable ionic liquid, and the upper-layer solution consists of bio-polyols which are extracted and are dehydrated by using the deionized water and alkaline water.

Preferably, the alkyl sulfonic acid is $C_nH_{2n}$, and the n is a positive integer within 3 to 6.

Preferably, the Brønsted strong acid is any one of phosphoric acid, sulfuric acid, methanesulfonic acid, benzenesulfonic acid, and p-toluenesulfonic acid.

Preferably, a molar ratio of the alkyl sulfonic acid in the Brønsted acid IL and the Brønsted strong acid is within 1.0 to 1.2.

Preferably, the epoxidized fatty acid esters are epoxide of fatty acid alkyl esters, the fatty acid alkyl esters are any one of biodiesel, unsaturated fatty acid alkyl esters, and a mixture of the biodiesel and the unsaturated fatty acid alkyl esters, wherein the biodiesel is fatty acid methyl ester which is transesterificated from vegetable oil, animal oil, and waste cooking oil, wherein the unsaturated fatty acid alkyl esters is any one or a mixture of more than two of alkyloleate, alkyl linoleate, and alkyllinolenate.

Preferably, the alcohols are any one of monohydric alcohol, polyols, and a mixture of the monohydric alcohol and the polyols, wherein monohydric alcohol are any one of methanol, ethanol, propanol, butanol, and isomer of the propanol, and the butanol, wherein the polyols are ethylene glycol, propylene glycol, butanediol, and isomer of the ethylene glycol, the propylene glycol and the butanediol, and glycerol.

Preferably, a reacting time of the ring-opening hydroxylation of the epoxidized biodiesel is within 1 to 20 hours, a reacting time of ring-opening hydroxylation of epoxidized fatty acid alkyl esters is within 4 to 24 hours, and a reacting time of ring-opening hydroxylation of the epoxidized biodiesel and the epoxidized fatty acid alkyl esters is within 1 to 20 hours.

Preferably, a molar ratio of the alcohols and the epoxidized fatty acid esters is within 4 to 12.

Preferably, a molar ratio of the Brønsted acid IL and the epoxidized fatty acid esters is within 0.05 to 0.12.

Preferably, a molar ratio of the Brønsted acid IL and the epoxidized fatty acid esters is within 0.05 to 0.10.

Preferably, a reacting temperature of ring-opening hydroxylation is within 40° C. to 80° C.

Preferably, a reacting temperature of ring-opening hydroxylation is within 40° C. to 60° C.

DETAILED DESCRIPTION OF THE PREFERRED EMBODIMENTS

A method of preparing bio-polyols from epoxidized fatty acid esters according to the present invention comprises steps of:

controlling a molar ratio of feeding alcohols and epoxidized fatty acid esters within 4 to 12;

controlling a molar ratio of catalyst and the epoxidized fatty acid esters within 0.01 to 0.15, wherein the catalyst is Brønsted acid IL;

reacting the alcohols, the epoxidized fatty acid esters, and the catalyst in a temperature of 40° C. to 80° C. for 1 to 24 hours in atmospheric environment;

extracting and layering crude products by using deionized water after reacting thealcohols, the catalyst, and the epoxidized fatty acid esters to acquire an upper layer and a lower layer, wherein the lower layer consists of ionic liquid and unreacted alcohols, and the ionic liquid and the unreacted alcohols are concentrated and dried to recycle reusable ionic liquid; wherein the upper layer consists of bio-polyols which are extracted by using the deionized water and alkaline water and then dehydrated, wherein a yield of the bio-polyols is 60% to 70% or more after analyzing the bio-polyols by using $^1$H Nuclear Magnetic Resonance ($^1$H NMR).

In a first embodiment, epoxy fatty acid methyl esters and monohydric alcohol are added into an reactor, wherein a molar ratio of the monohydric alcohol and the epoxy fatty acid methyl esters is within 4 to 10, and the catalyst, i.e., the Brønsted acid IL, is added to synthesize the monohydric alcohol and the epoxy fatty acid methyl esters, wherein a molar ratio of the catalyst and the epoxy fatty acid methyl esters is within 0.05 to 0.10, the epoxy fatty acid methyl esters, the monohydric alcohol, and the catalyst are reacted in a temperature of 40° C. to 60° C. for 4 to 20 hours; the crude products are extracted and layered by using the deionized water after reacting the epoxy fatty acid methyl esters, the monohydric alcohol, and the catalyst to acquire an upper layer and a lower layer, wherein the lower layer consists of reusable ionic liquid which is concentrated and is dried; wherein the upper layer consists of bio-polyols which are extracted by using the deionized water and weak alkaline water and then dehydrated, wherein a hydroxyl value is 179 mgKOH/g.

In a second embodiment, epoxy fatty acid methyl esters and polyols are added into an reactor, wherein a molar ratio of the polyols and the epoxy fatty acid methyl esters is within 4 to 8, and the catalyst, i.e., the Brønsted acid IL, is added to synthesize the polyols and the epoxy fatty acid methyl esters, wherein a molar ratio of the catalyst and the epoxy fatty acid methyl esters is within 0.05 to 0.10, the epoxy fatty acid methyl esters, the polyols, and the catalyst are reacted in a temperature of 40° C. to 80° C. for 1 to 20 hours; the crude products are extracted and layered by using the deionized water after reacting the epoxy fatty acid methyl esters, bio-polyols, and the catalyst to acquire an upper layer and a lower layer, wherein the lower layer consists of reusable ionic liquid which is concentrated and is dried; the upper layer consists of bio-polyols which are extracted by using the deionized water and weak alkaline water and then dehydrated, wherein a hydroxyl value is 309 to 322 mgKOH/g.

In a third embodiment, epoxidized methyl oleate and methanol are added into an reactor, wherein a molar ratio of the methanol and the epoxidized methyl esters oleate is within 4 to 10, and the catalyst, i.e., the Brønsted acid IL, is added to synthesize the epoxidized methyl oleate and the methanol, wherein a molar ratio of the catalyst and the epoxidized methyl oleate is within 0.05 to 0.10, the epoxidized methyl oleate, the methanol, and the catalyst are reacted in a temperature of 40° C. for 16 to 24 hours; the crude products are extracted and layered by using the deionized water after reacting the epoxidized methyl oleate, the methanol, and the catalyst to acquire an upper layer and a lower layer, wherein the lower layer consists of reusable ionic liquid which is concentrated and dried; the upper layer consists of bio-polyols which are extracted by using the deionized water and weak alkaline water and then dehydrated, wherein a hydroxyl value is 170 mgKOH/g.

In a fourth embodiment, epoxidized methyl oleate and polyols are added into an reactor, wherein a molar ratio of the polyols and the epoxidized methyl esters oleate is within 4 to 10, and the catalyst, i.e., the Brønsted acid IL, is added to synthesize the epoxidized methyl oleate and the polyols, wherein a molar ratio of the catalyst and the epoxidized methyl oleate is within 0.05 to 0.10, the epoxidized methyl oleate, the polyols, and the catalyst are reacted in a temperature of 40 to 80° C. for 4 to 20 hours; the crude products are extracted and layered by using the deionized water after reacting the epoxidized methyl oleate, the polyols, and the catalyst to acquire an upper layer and a lower layer, wherein the lower layer consists of reusable ionic liquid which is concentrated and is dried; wherein the upper layer consists of bio-polyols which are extracted by using the deionized water and the weak alkaline water and then dehydrated, wherein a hydroxyl value is within 319 to 408 mgKOH/g.

In a fifth embodiment, epoxidized fatty acid butyl esters and monohydric alcohol are added into an reactor, wherein a molar ratio of the monohydric alcohol and the epoxidized fatty acid butyl esters is within 6 to 12, and the catalyst, i.e., the Brønsted acid IL, is added to synthesize the epoxidized fatty acid butyl esters and the monohydric alcohol, wherein a molar ratio of the catalyst and the epoxidized fatty acid butyl esters is within 0.05 to 0.15, the epoxidized fatty acid butyl esters, the monohydric alcohol, and the catalyst are reacted in a temperature of 40 to 60° C. for 16 to 24 hours; the crude products are extracted and layered by using the deionized water after reacting the epoxidized fatty acid butyl esters, the monohydric alcohol, and the catalyst to acquire an upper layer and a lower layer, wherein the lower layer consists of reusable ionic liquid which is concentrated and dried to be recyclable; the upper layer consists of bio-polyols which are extracted by using the deionized water and the weak alkaline water and then dehydrated, wherein a hydroxyl value is within 263 to 293 mgKOH/g.

In a sixth embodiment, epoxidized fatty acid butyl esters and polyols are added into an reactor, wherein a molar ratio of the polyols and the epoxidized fatty acid butyl esters is within 6 to 12, and the catalyst, i.e., the Brønsted acid IL, is added to synthesize the epoxidized fatty acid butyl esters and the polyols, wherein a molar ratio of the catalyst and the epoxidized fatty acid butyl esters is within 0.05 to 0.15, the epoxidized fatty acid butyl esters, the polyols, and the catalyst are reacted in a temperature of 40 to 80° C. for 4 to 20 hours; the crude products are extracted and layered by using the deionized water after reacting the epoxidized fatty acid butyl esters, the polyols, and the catalyst to acquire an upper layer and a lower layer, wherein the lower layer consists of reusable ionic liquid which is concentrated and dried; and the upper layer consists of bio-polyols which are extracted by using the deionized water and the weak alkaline water and then dehydrated, wherein a hydroxyl value is within 204 to 269 mgKOH/g.

In a seventh embodiment, epoxidized fatty acid methyl esters and recycled ionic liquid is added into an reactor and is pre-heated to a temperature of 40° C., and polyols are added to react with the epoxy fatty acid methyl esters and recycled ionic liquid for 20 to 24 hours, wherein the crude products are extracted and layered by using the deionized water after reacting the epoxidized fatty acid butyl esters, the polyols and the recycled ionic liquid to acquire an upper layer and a lower layer, wherein the lower layer consists of reusable ionic liquid which is concentrated and dried; the upper layer consists of bio-polyols which are extracted by using the deionized water and the weak alkaline water and then dehydrated, and above-mentioned steps are executed repeatedly until a hydroxyl value is reduced. In this embodiment, reusable ionic liquid is used for three times, and hydroxyl values of the reusable ionic liquid used for three times are 286, 266, and 286 mgKOH/g respectively.

In an eighth embodiment, 1 to 10 units of foaming agents, 0.1 to 0.5 unit of tin catalyst, 0.1 to 1 unit of amine catalyst, 1 unit of surfactant are added into and are mixed with 100 units of bio-polyols of the second embodiment by ways of a mixing machine, then 50 units of hardeners are added into the container to mix with the foaming agents, the tin catalyst, the amine catalyst, the surfactant, and the bio-polyols, then the mixture are poured into a mold to react in a room temperature, thus acquiring polyurethane foaming material.

Thereby, the bio-polyols are made of raw material in a green manufacturing process. Preferably, the catalyst is the acidic ionic liquid to synthesize the epoxidized fatty acid esters and alcohols to cause hydroxylation, thus synthesizing bio-polyols to replace polyols and to made from polyurethane material, polyurethane foaming material, artificial leather, coating material, and adhesives. Preferably, the hydroxylation is included in the green manufacturing process and is extracted by using the deionized water and alkaline water, thus recycling the reusable ionic liquid and reducing pollution and corrosion.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. A method of preparing bio-polyols from epoxidized fatty acid esters comprising steps of:
    replacing amphoteric compound by using alkyl sulfonic acid, wherein the alkyl sulfonic acid are synthesized with Brønsted strong acid to produce Brønsted acid IL, a molar ratio of the alkyl sulfonic acid and the Brønsted strong acid is within 1.0 to 1.5;
    mixing the epoxidized fatty acid esters and the Brønsted acid IL at a predetermined ratio, adding alcohols for using as ring-opening reagent, thus producing reaction solution, wherein the reaction solution is heated within a temperature of 30° C. to 100° C. for 1 to 24 hours to cause ring-opening hydroxylation, wherein a molar ratio of the alcohols and the epoxidized fatty acid esters is within 4 to 20, and a molar ratio of the Brønsted acid IL and the epoxidized fatty acid esters is within 0.01 to 0.15; and
    extracting and layering the reaction solution by using deionized water to acquire upper-layer solution and lower-layer solution, wherein the lower-layer solution consists of ionic liquid which is concentrated and dried to recycle reusable ionic liquid, and the upper-layer solution consists of bio-polyols which are extracted by using the deionized water and alkaline water and then dehydrated.

2. The method as claimed in claim 1, wherein the alkyl sulfonic acid is $C_nH_{2n}$, and the n is a positive integer within 3 to 6.

3. The method as claimed in claim 1, wherein the Brønsted strong acid is any one of phosphoric acid, sulfuric acid, methanesulfonic acid, benzenesulfonic acid, and p-toluenesulfonic acid.

4. The method as claimed in claim 1, wherein a molar ratio of of the alkyl sulfonic acid in the Brønsted acid IL and the Brønsted strong acid is within 1.0 to 1.2.

5. The method as claimed in claim 1, wherein the epoxidized fatty acid esters are epoxide of fatty acid alkyl esters, the fatty acid alkyl esters are any one of biodiesel, unsaturated fatty acid alkyl esters, and a mixture of the biodiesel and the unsaturated fatty acid alkyl esters, wherein the biodiesel is fatty acid methyl ester which is transesterificated from vegetable oil, animal oil, and waste cooking oil, wherein the unsaturated fatty acid alkyl esters is any one or a mixture of more than two of alkyloleate, alkyl linoleate, and alkyllinolenate.

6. The method as claimed in claim 1, wherein the alcohols are any one of monohydric alcohol, polyols, and a mixture of the monohydric alcohol and the polyols, wherein the monohydric alcohol are any one of methanol, ethanol, propanol, butanol, and isomer of the methanol, the ethanol, the propanol, and the butanol, wherein the polyols are ethylene glycol, propylene glycol, butanediol, and isomer of the ethylene glycol, the propylene glycol and the butanediol, and glycerol.

7. The method as claimed in claim 5, wherein a reacting time of the ring-opening hydroxylation of epoxide of the biodiesel is within 1 to 20 hours, a reacting time of ring-opening hydroxylation of epoxide of the unsaturated fatty acid alkyl esters is within 4 to 24 hours, and a reacting time of ring-opening hydroxylation of epoxide of the biodiesel and the unsaturated fatty acid alkyl esters is within 1 to 20 hours.

8. The method as claimed in claim 1, wherein a molar ratio of the alcohols and the epoxidized fatty acid esters is within 4 to 12.

9. The method as claimed in claim 1, wherein a molar ratio of the Brønsted acid IL and the epoxidized fatty acid esters is within 0.05 to 0.12.

10. The method as claimed in claim 9, wherein a molar ratio of the Brønsted acid IL and the epoxidized fatty acid esters is within 0.05 to 0.10.

11. The method as claimed in claim 1, wherein a reacting temperature of ring-opening hydroxylation is within 40° C. to 80° C.

12. The method as claimed in claim 11, wherein a reacting temperature of ring-opening hydroxylation is within 40° C. to 60° C.

* * * * *